(12) United States Patent
Huthmacher et al.

(10) Patent No.: US 6,552,222 B2
(45) Date of Patent: Apr. 22, 2003

(54) HYDROLYSIS OF ACYLAMINO ACIDS

(75) Inventors: Klaus Huthmacher, Gelnhausen (DE); Christoph Weckbecker, Gründau-Lieblos (DE); Horst Weigel, Rodenbach (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/927,776

(22) Filed: Aug. 13, 2001

(65) Prior Publication Data

US 2002/0026076 A1 Feb. 28, 2002

(30) Foreign Application Priority Data

Aug. 11, 2000 (DE) .......................................... 100 39 268

(51) Int. Cl.[7] ...................... C07C 323/00; C07C 229/00; C07C 227/00; C07C 209/00
(52) U.S. Cl. ...................... 562/559; 562/516; 562/553; 562/556; 564/414
(58) Field of Search ................................ 562/516, 553, 562/554, 556; 564/414

(56) References Cited

U.S. PATENT DOCUMENTS

| | | | |
|---|---|---|---|
| 3,766,266 A | * | 10/1973 | Wakamatsu et al. |
| 5,656,757 A | * | 8/1997 | Jenczewski et al. |
| 6,255,529 B1 | * | 7/2001 | Nagase et al. |

OTHER PUBLICATIONS

Radzicka et al, Rates of Uncatalyzed Peptide Bond Hydrolysis in Neutral Solution and the Transition State Affinities of Proteases, Journal of the American Chemical Society, 1996, 118, pp. 6105–6109.*

The Merck Index 1983, Tenth edition, Merck &Co., Inc. Rahway, NJ, p. 88, entry 92 and p. 858, entry 5849.*

Rinderknecht et al, The Synthesis of 5–Fluoro–DL–Tryptophan, 1950, Journal of the American Chemical Society,72, pp. 2296–2297.*

Robert M. Williams, Glenn J. Fegley: "Asymmetric Synthesis of 1–Aminocyclopropane–1–carboxylic Acid Derivatives", J.Am. Chem. Soc., vol. 113, No. 23, 1991, pp. 8796–8806 XP–002183994.

W.S. Chilton, G. Tsou: "A Chloro Amino Acid from Amanita Solitaria" Phytochemistry, vol. 11, 1972, pp. 2853–2857 XP002183995.

Database Crossfire Beilstein Online!Beilstrein Institut zur Forderung der Chemischen Wissenschaften, Frankfurt am Main, DE; XP002183996.

Thomas N. Wheeler, John A. Pay: "A Convenient and Efficient Synthesis of 1–Aminocyclopropanecarboxylic Acid", Synthetic Communication, vol. 18, No. 2, 1988, pp. 141–150, XP001022909.

* cited by examiner

*Primary Examiner*—Joann Ricater
*Assistant Examiner*—Paul A. Zucker
(74) *Attorney, Agent, or Firm*—Smith, Gambrell & Russell, LLP

(57) ABSTRACT

A process for the preparation of racemic amino acids, characterized in that an acylamino acid of the formula $$R^1—CH(NH—CO—R^2)COOH$$

wherein $R^1$ is hydrogen, a linear, branched or cyclic alkyl that has from 1 to 7 carbon atoms and that may contain substituents such as a hydroxyl, alkyloxy or alkylthio group; and $R^2$ is a hydrogen atom or an alkyl having from 1 to 3 carbon atoms; is heated in the presence of water, in a pressure-resistant vessel, to a temperature in the range from 110° C. to 220° C. and is hydrolyzed.

20 Claims, No Drawings

HYDROLYSIS OF ACYLAMINO ACIDS

INTRODUCTION AND BACKGROUND

The present invention relates to a process for the preparation of amino acids, particularly by hydrolysis of acylamino acids.

Amino acids are used in human medicine and in the pharmaceuticals industry, in the foodstuffs industry and, very particularly, in the feeding of animals. Amino acids can be in enantiomerically pure form, but also in the form of the racemate. Amino acids are also used in the synthesis of numerous fine chemicals and active ingredients.

Various processes are available for the industrial production of amino acids, such as the hydrolysis of proteins, the Strecker process, biotechnological processes and amidocarbonylation.

The reaction known as amidocarbonylation is the conversion of carbonyl compounds or alkenes with acylamides as the nitrogen source and carbon dioxide or synthesis gas. The first products of that reaction are not the free amino acids, but the N-acylamino acids. Such N-acylamino acids are valuable starting materials for the enzymatic racemate cleavage for the preparation of enantiomerically pure amino acids (Beller et al., Chem. Eur. J. 1998. 4, 935–941).

It is, however, not important to use an enantiomerically pure form in all applications of amino acids. There is also a need for racemic amino acids. An example thereof is D,L-methionine, a racemic amino acid, which is used in large amounts as a feed additive for animals and poultry.

The hydrolysis of acylamino acids to amino acids is usually carried out by reaction with aqueous lye or mineral acid in at least equimolar amounts. Examples thereof are given, for example, in an article by J. F. Knifton (Catalysis Today, 18 (1993) 355–384). In order to isolate the amino acid, the lye or mineral acid that has been added must then be neutralized once the reaction is complete. Owing to the in some cases good solubility of amino acids and the salts in water formed on neutralization, the separation from the salt on isolation of the pure amino acids is often associated with considerable expense and losses. When ion exchangers are used, salt formation is not avoided but simply moved to a different process stage. The large amount of salt that is inevitably formed in that process is highly disadvantageous for an industrial application from an ecological and an economic point of view.

It is also known that amides can be hydrolyzed with water in the region of the critical point (374° C., 218 atm) without the addition of acids or lyes. Under such conditions, however, the technical requirements are considerable. The reaction medium is highly corrosive in that temperature range and high-quality materials are therefore required for the construction of reaction equipment.

In consideration of the prior art outlined and discussed above, it is an object of the present invention to find a further process for the preparation of racemic amino acids from acylamino acids, in which the amino acids can readily be isolated and the formation of large amounts of salts is avoided.

SUMMARY OF THE INVENTION

The above and other objects of the present invention can be achieved by a process for the preparation of racemic amino acids, wherein an acylamino acid of the general formula $$R^1\text{—CH(NH—CO—}R^2\text{)COOH}$$

wherein $R^1$ is hydrogen, linear, branched or cyclic alkyl that has from 1 to 7 carbon atoms and that may contain substituents such as a hydroxyl, alkyloxy or alkylthio group; and $R^2$ is a hydrogen atom or an alkyl having from 1 to 3 carbon atoms;
is heated in the presence of water, in a pressure-resistant vessel, to a temperature in the range from 110° C. to 220° C. and is hydrolyzed.

It has been found that acylamino acids can also be hydrolyzed in a temperature range that is markedly below the critical temperature without the addition of acids or bases.

DETAILED DESCRIPTION OF THE INVENTION

An important aspect according to the present invention is that the required temperature range that is necessary in the process according to the invention is markedly below the critical temperature, which means that the demands made of the materials and the required pressure resistance of the reaction vessel lie within normal limits.

In particular and surprisingly, it has now been found that the process according to the invention may preferably be carried out in such a manner that the desired racemic amino acids can be prepared without the aid of further substances and can then be obtained from the aqueous reaction solution with purities of >95% with, at the same time, a very high degree of selectivity.

In a preferred embodiment of the process of the invention, the hydrolysis is carried out at temperatures from 110° C. to 220° C., preferably from 140° C. to 200° C., particularly preferably from 140° C. to 180° C.

Racemic amino acids prepared in that manner are of high purity and can be used for many applications without further purification.

Suitable acylamino acids are compounds of the general formula $R^1$—CH(NH—CO—$R^2$)COOH wherein $R^1$ is hydrogen, a linear, branched or cyclic alkyl that has from 1 to 7 carbon atoms and that may contain substituents such as a hydroxyl, alkyloxy or alkylthio group. $R^2$ represents a hydrogen atom or an alkyl having from 1 to 3 carbon atoms.

Examples of linear, branched or cyclic alkyls are methyl, ethyl, propyl, isopropyl, 1-methylpropyl, 2-methylpropyl, butyl and cyclohexyl, with alkyls having from 1 to 5 carbons being preferred. Such alkyls may be substituted by from 1 to 3 amino, hydroxyl, halogen, alkyloxy, alkylthio, urea or carboxy groups.

According to the invention, the acylamino acid to be hydrolyzed is heated together with water in a pressure-resistant vessel. The pressure that builds up corresponds to the vapor pressure of the water at the corresponding temperature.

The hydrolysis may be carried out continuously or discontinuously.

The amount of water required is dependent on the nature of the acylamino acid and is generally in a range from 0.3 to 2.0 liters (l), preferably from 0.5 to 1.5 l/mol of acylamino acid. The reaction time required for complete conversion is affected by the amount of water, an increase in the amount of water shortens the reaction time. It is also advantageous during the reaction to remove from the equilibrium by distillation the carboxylic acid that forms, or a portion thereof. However, it is also possible to separate off the carboxylic acid once the reaction is complete.

When the reaction is complete, the reaction solution contains, in addition to small residual amounts of the acylamino acid that was used, the amino acid that has formed, the carboxylic acid analogous to the acyl group used, and traces of condensation products. Isolation of the amino acid from the reaction solution may be effected by various methods known per se, the method depending on the solubility of the amino acid and the properties of the carboxylic acid. Before or after separation of the amino acid, or of a portion thereof, in the form of a crystallisate, the carboxylic acid is largely separated off by distillation, azeotropic distillation or extraction. Ketones, such as methyl isobutyl ketone, or ethers, such as methyl tert-butyl ether, may be used as the extracting agent.

For separation of the amino acid in the form of a crystallisate, the solution, particularly in the case of readily soluble amino acids, may be concentrated. The filtrate obtained after separation of the solids is a saturated aqueous solution of the amino acid and may be used in the hydrolysis again together with fresh acylamino acid.

The Examples which follow are intended to illustrate the invention, without having a limiting effect.

EXAMPLE 1

A mixture of 19.1 grams (g) of N-acetyl-D,L-methionine and 150 milliliters (ml) of water was heated for 1 hour at 180° C. in a laboratory autoclave. After cooling to room temperature, 6.1 g of crystalline methionine (content, determined by HPLC: 99.7%) were obtained. A further 5.9 g of methionine and 3.4 g of acetyl-methionine were contained in the filtrate. The conversion of the acetyl compound was 82.2%, the selectivity of the reaction was 97.8%.

EXAMPLE 2

A metering pump was attached to a laboratory autoclave having a volume of 250 ml, and a condenser was attached downstream of a valve. The autoclave was filled with 20 g of acetylmethionine and 150 ml of water and heated to 160° C., with stirring. At 20-minute intervals, the valve was opened slightly until in each case 20 ml of condensation product of water and acetic acid were obtained. The level in the autoclave was kept constant by pumping in the same volume of water. The internal temperature was in the range from 140° C. to 160° C. for 4 hours. After cooling to 20° C., 8.2 g of pure methionine were filtered off. The filtrate contained a further 5.1 g of methionine and 2.7 g of acetyl-methionine. The conversion was 86.5%, the yield was 85.1%, which corresponded to a selectivity of 98.3%.

EXAMPLE 3

A mixture of 15.9 g of N-acetyl-D,L-valine and 150 ml of water was heated for 2 hours at 180° C. in an autoclave having a volume of 250 ml. Subsequent analysis (HPLC) showed, at a conversion of 84.7%, a yield of 83.5%, which corresponded to a selectivity of 98.5%.

Further variations and modifications of the foregoing will be apparent to those skilled in the art and are intended to be encompassed by the claims appended hereto.

German application 100 39 268.7 is relied on and incorporated herein by reference.

We claim:

1. A process for the preparation of methionine, consisting essentially of heating acetyl methionine in the presence of water in a hydrolysis reaction
in a pressure-resistant vessel, to a temperature in the range from 110° C. to 220° C. and hydrolyzing said acetyl methionine in the hydrolysis reaction to obtain said methionine.

2. The process according to claim 1, wherein the hydrolyzing is carried out in a temperature range from 140° C. to 200° C.

3. The process according to claim 2, wherein the hydrolyzing is carried out in a temperature range from 140° C. to 180° C.

4. The process according to claim 1, wherein a carboxylic acid corresponding to the acyl group of the methionine is formed in the hydrolysis reaction, and at least a portion of said carboxylic acid is removed from the reaction solution during the reaction or after the reaction is complete.

5. The process according to claim 2, wherein a carboxylic acid corresponding to the acyl group of the methionine is formed in the hydrolysis reaction, and at least a portion of said carboxylic acid is removed from the reaction solution during the reaction or after the reaction is complete.

6. The process according to claim 3, wherein a carboxylic acid corresponding to the acyl group of the methionine is formed in the hydrolysis reaction, and at least a portion of said carboxylic acid is removed from the reaction solution during the reaction or after the reaction is complete.

7. The process according to claim 1, wherein after the reaction is complete, the methionine is separated in the form of a solid.

8. The process according claim 2, wherein, after the reaction is complete, the methionine is separated in the form of a solid.

9. The process according to claim 3, wherein, after the reaction is complete, the methionine is separated in the form of a solid.

10. The process according to claim 7 further comprising recycling filtrate obtained in separating off the amino acid.

11. A process for the preparation of a high purity methionine, consisting essentially of reacting acetyl methionine in a hydrolysis reaction by heating in the presence of water, in the range of 0.3 to 2 liters of water per mol of acetyl methionine, to a temperature in the range from 110° to 220° and thereby hydrolyzing the acetyl methionine.

12. The process according to claim 11, wherein the hydrolysis is carried out in a temperature range from 140° C. to 200° C.

13. The process according to claim 12, wherein the hydrolysis is carried out in a temperature range from 140° C. to 180° C.

14. The process according to claim 11, wherein carboxylic acid formed in the hydrolysis reaction is at least partially removed from the reaction solution during the reacting or after reacting is completed.

15. The process according to claim 11, after the reacting is complete, amino acid formed is separated off in the form of a solid, and filtrate is recycled.

16. A process for the production of methionine by hydrolysis comprising forming a reaction solution of acetyl methionine in water, heating said reaction solution in a pressure-resistant vessel, to a temperature in the range from 110° C. to 220° C. for a sufficient period of time to achieve hydrolysis to obtain said methionine.

17. The process according to claim 16, wherein the hydrolysis is carried out in a temperature range from 140° C. to 200° C.

18. The process according to claim 17, wherein the hydrolysis is carried out in a temperature range from 140° C. to 180° C.

19. The process according to claim 16 wherein a carboxylic acid is formed in the hydrolysis, and at least a portion thereof is removed from the reaction solution during the reaction or once the reaction is complete.

20. The process according to claim 16 wherein once the reaction is complete, the methionine is separated off in the form of a solid, and the filtrate is recycled.

* * * * *